United States Patent
Tikhonov et al.

(10) Patent No.: US 8,092,845 B2
(45) Date of Patent: Jan. 10, 2012

(54) ANTI-INFLAMMATORY EXTRACT AND AGENT AND METHOD FOR THE PRODUCTION THEREOF

(75) Inventors: Vladimir Petrovich Tikhonov, Moscow (RU); Valery Gennadievich Makarov, St. Petersburg (RU); Lyudmila Konstantinovna Gavrovskaya, St. Petersburg (RU)

(73) Assignee: Otkrytoe Aktsionernoe Obschestvo Zavod Ekologicheskoy Tekhniki I Ekopitaniya "Diod", Moscow (RU)

( * ) Notice: Subject to any disclaimer, the term of this patent is extended or adjusted under 35 U.S.C. 154(b) by 649 days.

(21) Appl. No.: 11/719,457

(22) PCT Filed: Nov. 15, 2005

(86) PCT No.: PCT/RU2005/000567
§ 371 (c)(1), (2), (4) Date: Sep. 27, 2007

(87) PCT Pub. No.: WO2006/054921
PCT Pub. Date: May 26, 2006

(65) Prior Publication Data
US 2009/0142419 A1 Jun. 4, 2009

(30) Foreign Application Priority Data
Nov. 16, 2004 (RU) ................. 2004133285

(51) Int. Cl.
*A61K 36/906* (2006.01)
*A61K 36/15* (2006.01)

(52) U.S. Cl. ........................................ 424/756; 424/770

(58) Field of Classification Search ........................ None
See application file for complete search history.

(56) References Cited

U.S. PATENT DOCUMENTS

| | | | |
|---|---|---|---|
| 5,494,668 A | 2/1996 | Patwardhan | |
| 5,536,506 A | 7/1996 | Majeed et al. | |
| 5,888,514 A | 3/1999 | Weisman | |
| 6,534,086 B1 * | 3/2003 | Krumhar | 424/464 |
| 2002/0010168 A1 * | 1/2002 | Ammon et al. | 514/198 |

FOREIGN PATENT DOCUMENTS

| | | | |
|---|---|---|---|
| CN | 1110158 A | * | 10/1995 |
| EP | 1088552 A1 | * | 4/2001 |
| KR | 1020040078498 | * | 9/2004 |
| KR | 20040078498 A | | 10/2004 |
| RU | 2141336 | | 11/1999 |
| WO | 0062751 A2 | | 10/2000 |
| WO | 01195727 | | 12/2001 |

OTHER PUBLICATIONS

Vegetable Oils and Fats. Retrieved from the internet. Retrieved on Apr. 6, 2010. <http://en.wikipedia.org/wiki/Vegetable_fats_and_oils>. pp. 1-9.*
Ansel et al. Pharmaceutical Dosage Forms and Drug Delivery Systems. Seventh Edition. 1999. p. 180.*
Viable-herbal.com. Web archive date Jan. 24, 2000. Retrieved from the internet <http://web.archive.org/web/20000124113842/http://viable-herbal.com/herbology1/herbs42.htm>. Retrieved on Apr. 6, 2010. pp. 1-4.*
www.goldenoils.co.uk. Retrieved form the internet on Apr. 6, 2010. <http://www.goldenoils.co.uk/pinenutoil.htm>. p. 1.*
Nelson et al. Strong Women and Men Beat Arthritis: The Scientifically Proven Program That Allows People With Arthritis to Take Charge of Their Disease. Penguin 2003. p. 45.*
PCT Patent Application No. PCT/RU2005/000567, International Search Report dated Apr. 6, 2006, p. 2.
Shrikhande et al., "Development and Evaluation of Anti-Inflammatory Oleogels of *Bosewellia serrata* (GUGUL) and *Curcuma longa* (Turmeric)", Indian Drugs, XX, XX, vol. 38, No. 12, Dec. 1, 2001, pp. 613-616, XP008005371.
Darshan et al., "Patented antiinflammatory plant drug development from traditional medicine", Phytotherapy Research 200405 GB, vol. 18, No. 5, May 2004, pp. 343-357, XP002479924.
European Patent Application No. 05818197.5 Search Report dated May 29, 2009.
European Patent Application No. 05818197.5, Communication dated Jun. 15, 2010.
Rasatantrasarah Evam Siddhaprayogasamgrahah, Part 1, Krishan Gopal Ayurveda Bhawan, 8th Edition, 1990, pp. 492-493, Formulation ID: RS22/714, Formulation Name: Pramehantaka Vati 01.
Al-Qaanoon-fil-Tibb, vol. II by Abu Ali Ibn-e-Sina, (11th century AD), Institute of History of Medicine and Medical Research, Jamia Hamdard, New Delhi-62, pp. 1987 AD, pp. 351-352, Formulation ID: AH1/617, Formulation Name: Kundur.
Siddhabhesajamanimalah by Krsnarama Bhatta, Commentary by Kaladhara Bhatta, Chaukhambha Krishnadas Academy, Varanasi, 3rd Edition, 2003, pp. 371-372, Formulation ID: RS4/1235, Formulation Name: Malla Vati-1.
Sahastrayoga, Translated by D.V. Panditarao: Central Council for Research in Ayurveda & Siddha, New Delhi, 1990, p. 229, Formulation ID: VS/3550.

* cited by examiner

*Primary Examiner* — Melenie McCormick
(74) *Attorney, Agent, or Firm* — Gail C. Silver; Borden Ladner Gervais LLP

(57) ABSTRACT

The invention relates to the pharmaceutical industry, in particular to producing herbal remedy for integrally treating various inflammatory diseases. The inventive remedy comprises a dry *Boswellia* extract dissolved in the oil extract of Siberian stone pine seeds and *Curcuma*. The remedy can be used in the form of soft gelatine capsules for peroral administration, wherein lecithin, hydroxy-toluene butyl, alpha-tocopherol acetate, ascorbyl palmitate are added to the ready-for-use oil extract. The inventive method for producing said remedy consists in producing the oil extracts of Siberian stone pine seeds and *Curcuma* and in subsequently adding the dry *Boswellia* extract thereto.

6 Claims, No Drawings

ANTI-INFLAMMATORY EXTRACT AND AGENT AND METHOD FOR THE PRODUCTION THEREOF

FIELD OF INVENTION

The invention relates to biologically active agents from vegetable raw material and can be used in complex therapy of different inflammatory diseases as well as an agent increasing non-specific resistance of the organism.

PRIOR ART

Modern anti-inflammatory agents are represented by two major groups being steroid and non-steroid pharmaceutical preparations.

The mechanism of action of steroidal preparations (glucocorticoids) encompasses the inhibition of phospholipase A2, that prevents the formation of eicosanoids which are the main tissue regulators and mediators in the inflammatory process (prostaglandins and leukotriens).

The action of non-steroid preparations is directed to the suppression of the activity of cyclooxigenase, which results in a decrease of prostaglandin and thromboxan formation and thus in a reduction of the inflammation.

Despite the evident anti-inflammatory activity of either preparation, there are several limitations for their long-term application due to the unfavourable side effects, the most important of which is a damage of the gastrointestinal tract, i.e. nausea, vomiting, stomach ulcer.

Moreover, these preparations can cause dysfunctions of the liver and kidney as well as bleedings, leukopenia to the extent of agranulocytosis, anemia. Changes in the central nervous system are also caused, such as giddiness, headaches, excitation, insomnia, fatigability, edema. All these factors limit the application of both steroid and non-steroid preparations in practical medicine, thus there is still a current need to search for new low-toxic anti-inflammatory preparations. Preparations of natural origin satisfy these requirements most of all.

In folk medicine, vegetable extracts in the form of infusions, tinctures, compresses or alcohol unctions are used for treating junction pain of any origin. For this purpose, wild rosemary, bourtree, melilot, origanum, nettle, burdock, juniper, tansy, couch-grass, pine, violet, horse-tail, hop, thyme, bur-marigold, eucalyptus, ginger or birch buds are used. Based on these and other herbs, several biologically active food additives have been developed such as Antiartrol, Bambuflex, Dokholodan (Дохо Ло Дан Ь), Epam-31, burdock root, Art, Joint Flex and others (see Federal register of biologically active food additives, Moscow, 2000, Chapter 10). They all are recommended as anti-inflammatory and tonic agents regulating processes in bone and cartilage tissue in the case of arthropathies.

Among certified anti-inflammatory preparations of natural origin are at present Aescusan, Romasulan, Tycveol, Calendeel, Traumeel, etc. Nevertheless, there remains a current need for developing anti-inflammatory agents for treating arthropathies.

In the traditional Indian medicine "ayurveda", the resin of the sacred (incense) tree *Boswellia serrata* has long since been used as an anti-inflammatory agent for treating arthritis, osteoarthrosis, inflammatory diseases of the lung and the intestine. The main active principle of this resin are boswellian acids. Studies on the alcohol and chloroform extracts of this resin and on individual boswellian acids have shown a significant decrease in the content of anti-inflammatory mediators under their action (mainly due to the inhibition of lipooxigenases which impedes the inflammation process [Sharma M. L., Bani S., Singh G. B., 1989, In Immunopharmacol 11(6): 647-652]).

Along with an anti-inflammatory action, Sharma M. L. and several other authors have revealed an analgetic, antipyretic, immunomodulating, antibacterial, hepatoprotecting, antihyperlipidemic action of the boswellian acids.

Known is the use of tetrahydropiperine and its analogues as an anti-inflammatory agent in an anti-tumor composition which contains curminoids. The composition may also contain extracts of turmeric, *Boswellia* and other vegetable components (US 2002/0058695, published in 2004).

A food additive is known which contains an extract of the pepper fruit as an obligatory component of the composition. It is also noted that the pepper fruit extract is used as a booster of the absorption of substances such as boswellin or an alcohol extract of *Bosewllia, curcumin* or an alcohol extract of *Curcuma longa*, pine bioflavonoid complex, vitamins E and C. Said additive is provided in an encapsulated form (U.S. Pat. No. 5,536,506, published in 1996).

A dietary additive is known having anti-inflammatory, analgetic, protective and antioxidative properties. Said additive contains resveratrol stilbene glucoside which is produced by different families of plants, *Curcuma* extract and additionally *Boswellia* extract. Data concerning the use of oil extracts of the plants mentioned above are not available (PCT application WO 0195727, published in 2001).

Known is a composition suitable for use in the oral cavity, based on a *Boswellia* extract or on boswellian acid or its derivatives, in an aromatic carrier like lemon oil or mint oil. Mentioned is also another possible use of the composition with administration of additional anti-bacterial or anti-inflammatory agents or vitamins. However, *Curcuma* and pine extracts are not mentioned (PCT application WO 0062751).

Due to the fact that the mechanism of action of boswellian acids is realized mainly by inhibiting the lipoxygenases which prevent the formation of inflammatory tissue regulators, as it has been shown by previous studies, and considering that prostaglandins and free radical processes play a comparably important role in inflammation mechanism, it is worthwhile, in order to increase the positive effect of the treatment, to produce a complex agent by additionally including other biologically active substances which can provide a more pronounced anti-inflammatory and tonic effect.

DISCLOSURE OF THE INVENTION

It is an object of the present invention to provide an agent having a wide spectrum of pharmacological action in order to allow a combination therapy of inflammatory diseases of different aetiology and to increase the protective functions of an organism.

The present invention provides an anti-inflammatory extract which contains a dry *Boswellia* extract or the derivatives thereof comprised in a vegetable oil carrier at the following ratio of the components:

| | |
|---|---|
| dry *Boswellia* extract or the derivatives thereof | up to 40 g |
| vegetable oil carrier | up to 100 ml. |

Another aspect of the present invention is an anti-inflammatory agent which contains the dry *Boswellia* extract comprised in a vegetable oil extract produced from Siberian stone pine seeds and *Curcuma* roots at the following ratio of the components:

| | |
|---|---|
| dry *Boswellia* extract | 5-40 g |
| oil extract of Siberian stone pine seeds and *Curcuma* roots | up to 100 ml. |

Said agent is provided in form of soft gelatinous capsules.

The method for the production of the anti-inflammatory agent comprises soaking intact Siberian stone pine seeds in a water-alcoholic solution, mixing said seeds with a vegetable oil at a volume ratio not more than 1:20 with subsequent extraction, thus obtaining a pine seed oil extract, pre-grinding and screening *Curcuma* roots, mixing said roots with the pine seed oil extract at a volume ratio not more than 1:10, and extracting to obtain a pine seed and *Curcuma* root oil extract, adding a dry *Boswellia* extract in an amount of 5-40 g per 100 ml of the oil extract and holding said mixture until complete dissolution of the desired product.

The extraction of the components is carried out by means of a rotary-pulsation method at a temperature not more than 50° C. and is followed by settling and filtering the oil extracts.

Another aspect of the present invention is an anti-inflammatory agent, wherein a gelatine capsule contains lecithin, butyl hydroxy toluene, alpha-tocopherol acetate, ascorbyl palmitate, dry *Boswellia* extract in a Siberian stone pine seed and *Curcuma* root oil extract at the following ratio of the components, in mg/capsule:

| | |
|---|---|
| dry *Boswellia* extract | 25-35 |
| Siberian stone pine seed and *Curcuma* root oil extract | 250-280 |
| alpha-tocopherol acetate | 0.30-0.35 |
| ascorbyl palmitate | 0.75-0.85 |
| lecithin | 0.15-0.25 |
| butyl hydroxy toluene | 0.01-0.02. |

The above-described agent can be used as a biologically active additive.

PREFERRED EMBODIMENT OF THE INVENTION

The above-described extract possesses pronounced anti-inflammatory activity and simultaneously supports an increase in the non-specific resistance of the organism.

The anti-inflammatory extract is obtained by the dissolution of the dry *Boswellia* extract in an oil carrier, in particular corn, soybean, sunflower, or other oils at a volume ratio of dry extract to oil carrier of (2-40): 100. Studies of the properties of the extract were performed with the application of Boswellik—a dry extract from *Boswellia serata*, dissolved in corn oil.

Diclofenac was used for the comparison of the therapeutic activity of Boswellik. Studies were performed on both male and female nondescript mice after oral administration of the preparations.

The results of studying the anti-exudative, analgesic and ulcerogenic actions of the extract indicate that Boswellik possesses therapeutic activity, similar to that of Diclofenac. The most pronounced anti-inflammatory properties of Boswellik are obtained at optimum doses of 100 and 130 mg/kg (1/20 of $IC_{50}$). Boswellik does not show an irritant effect on the gastrointestinal tract in contrast to Diclofenac and is superior to it concerning the tolerance index (ratio of the toxic and ulcerogenic doses) by 371 times. Boswellik is safe during long-term administration in contrast to Diclofenac, since the safety index which is the ratio of ulcerogenicity/efficacy for the first is 0, whereas for the second it ranges from 4.3 to 9.9.

Study of the Anti-Inflammatory Activity of Boswellik in a Model of Influence on the Acute Exudative Inflammation (Peritonitis) in Rats and Mice The evaluation of the anti-inflammatory activity for Boswellik has been carried out in a model of the acute inflammatory process—peritonitis—in rats and mice, caused by the intraperitoneal injection of acetic acid. Boswellik demonstrated the most pronounced anti-exudative effect in doses of 100 and 130 mg/kg.

Diclofenac at the dose of 8 mg/kg and Boswellik at doses of 10, 30 and 260 mg/kg had a considerably weaker influence on the volume of the inflammatory exudate in the abdominal cavity of the animals. An effective dose of Boswellik—130 mg/kg—has been determined on the basis of the obtained results.

Data relating to the evaluation of the anti-exudative effect of Boswellik are shown in Tables 1 and 2.

TABLE 1

Evaluation of the anti-exudative effect of Boswellik in a model of peritonitis in rats

| Experimental groups of animals n = 10 | Volume of the peritoneal exudate, µl | Degree of the anti-exudative effect A = [Ro − Rk]/Rk100% |
|---|---|---|
| Control | 4440 ± 310 | 0 |
| Diclofenac 8 mg/kg | 3350 ± 220* | 24 |
| Boswellik 10 mg/kg | 4100 ± 150 | 8 |
| Boswellik 30 mg/kg | 3770 ± 140 | 15 |
| Boswellik 100 mg/kg | 2780 ± 150* | 37 |
| Boswellik 130 mg/kg | 2270 ± 250* | 49 |
| Boswellik 260 mg/kg | 2980 ± 360* | 33 |

Note:
Significant deviation from control $p < 0.05$.

TABLE 2

Evaluation of the anti-exudative effect of Boswellik in a model of peritonitis in mice

| Experimental groups of animals n = 10 | Volume of the peritoneal exudate, µl | Degree of the anti-exudative effect A = [Ro − Rk]/Rk100% |
|---|---|---|
| Control | 240 ± 10 | 0 |
| Diclofenac 8 mg/kg | 37 ± 2* | 85 |
| Boswellik 30 mg/kg | 45 ± 4 | 81 |
| Boswellik 130 mg/kg | 29 ± 2* | 88 |
| Boswellik 260 mg/kg | 147 ± 6* | 39 |

Note:
Significant deviation from control $p < 0.05$.

Furthermore, in in vitro experiments on isolated human blood cells specific immunomodulating influence on the synthesis of immunoglobulins for the investigated preparations (Boswellik and Diclofenac) has been revealed.

The oil solution of Boswellik increases the spontaneous and activated synthesis of IgG at the dose of 260 µg/ml. It also increases the spontaneous and activated synthesis of IgA at doses of 10-30 µg/ml. It does not influence the synthesis of IgM, IgG1 and IgG4.

The anti-inflammatory effects of boswellic acids are due to the suppression of the activity of 5-lipooxigenase (5-LOG) and reduction in the synthesis of leucotrienes. Literature data confirm that the effect of Boswellik on the synthesis of immunoglobulins may also be the result of the effect of the boswellic acids on the activity of 5-lipooxigenase (5-LOG) and the synthesis of leucotrienes.

The effect of Boswellik on the synthesis of immunoglobulins may occur both via direct influence on B-lymphocytes producing them and indirectly, by action on macrophages, since leucotrienes and 5-LOG play an important role in the physiology of both B-lymphocytes and macrophages.

The present anti-inflammatory agent may also be used for increasing the non-specific resistance of the organism and as a biologically active food additive in order to increase the protective functions of the organism.

The composition of the present agent is developed on the basis of the analysis of the pharmacological action of its components and long-term own experience in creating agents of natural origin. The quantitative ratio of the ingredients is found empirically and is substantiated by experimental studies on animals.

As can be seen from the composition of the present agent, a relatively high amount of Siberian stone pine seed and *Curcuma* root oil extract is used for its preparation beside the *Boswellia* dry extract. The selection of the seeds of Siberian stone pine tree has been made on the basis of the long-term experience of their application in folk medicine, their high biological activity, and also on the basis of the experience of their use in compositions of medicines developed by us which are widely utilized in practical medicine.

The medicinal properties of the Siberian stone pine seeds are known from the XIth century: even Avicenna recommended to administer them with honey for treating stones and ulcers. In Russia, the broth and the alcohol tincture of the shells of the pine seeds were used for treating rheumatism, gout and arthritis, the infusion was used for treating neuroses, diseases of the kidneys and the liver as well as haemorrhoids. From the kernel of the seeds (nuts), a high-calorie milk and "vegetable cream" were prepared, which were used for treating pulmonary tuberculosis, diseases of the kidney, the bladder, and also as an overall-strengthening agent.

The study of the chemical composition of the pine seeds revealed the following: a wide complex of biologically active materials being proteins containing 14 amino acids, 70% of which are essential, vitamins A, E, B1, fatty acids, fatty oils, and microelements (Mg, Mn, Fe, Co, Cu, J, P). No other known vegetable raw material has such a set of useful substances. We have used kedrol, a Siberian stone pine oil extract obtained with a corn oil as a component of the agent according to the invention. The pharmacological action of said extract comprises soft strengthening, antioxidant, bactericide, wound-healing and other useful properties, which adds a strengthening action to the anti-inflammatory action of boswellic acids.

The composition of the agent also comprises *Curcuma longa* (tumeric), a perennial plant from the family of ginger. The main biologically active material of tumeric is curcumin, which is mostly localized in its roots and rhizome. The anti-inflammatory activity of curcumin and its derivatives is attributed to the presence of hydroxyl and phenol groups in the molecule, which participate in the inhibition of lipooxigenases. Besides the direct effect of curcumin on the pathogenetic mechanisms of inflammation, in experiments on animals a number of other positive pharmacological properties has been established: it contributes to the protection of the liver of animals under different hepatotoxic influences. The hepatoprotective effect of curcumin is explained by its antioxidative properties, which increase the protective functions of the organism. The suppression of stress-caused ulceration in the stomach under the action of curcumin is known. There is evidence for the presence of anticarcinogenic, hypocholesterinemic, antihypertensive, antibacterial, and antiviral activity in *Curcuma* extracts, which is a perfect complementation to its anti-inflammatory action. It is considered that the *Curcuma* roots oil extract is one of the most promising sources to increase the non-specific resistance of the organism.

Thus, the agent according to the present invention contains components with potential anti-inflammatory and over-all strengthening action.

The present agent is produced as follows.

The technology of producing the oil extract includes the following basic steps:

vegetable oil extraction of intact Siberian stone pine (SSP) seeds (after preliminary soaking of seeds with 50% ethyl alcohol) at a ratio of SSP:vegetable oil which is not more than 1:20 for at least 20 minutes using the rotary-pulsating technique;

extraction of the preliminarily grinded and screened *Curcuma* roots with the SSP oil extract for 1.5-2 hours under stirring (300 rpm) and heating up to 40° C. at a ratio of *Curcuma* roots:SSP extract which is not more than 1:10;

dissolution of the *Boswellia* dry extract (with a content of boswellic acids of at least 80%) in the SSP and *Curcuma* root oil extract at room temperature and holding the mixture for 12 hours (until complete dissolution). The oil extracts are studied with respect to the following parameters: visual appearance (transparent), thermostability (by level of the peroxide number—ALL-UNION STATE STAN. 26593) and the characterisation of the essential groups of the active substances.

For the analysis of individual boswellic acids, flavonoids and diterpenoids, the method of Reversed Phase Liquid Chromatography is used. The wavelength for detection of boswellic acids is 254 nm. The wavelengths for the UV-detection of diterpenoids and flavonoids (in the SSP oil extract) are 254 and 289 nm, respectively. The calculation of the overall content of curcuminoids in relation to the curcumin is carried out by the method of direct spectrophotometry at a wavelength of 425 nm using a standard sample of curcumin.

In the animal tests, experimental studies on the present agent have been carried out in order to reveal the presence of specific pharmacological activity.

Study of Antiinflammatory Activity in a Model of Carrageen-Induced Rat Paw Edema Experiments were carried out on male nondescript rats (180-200 g). Each experimental group comprised 10 individuals. Acute inflammatory reaction (edema) was caused by subplantar administration of 0.1 ml of 1% solution of carrageenine. All substances being investigated (present agent at several doses) were administered per os in a volume of 0.3 ml according to the following regimen of administration: 2 days prior to inflammation one time per day and on the $3^{rd}$ day 4 hours prior to the administration of carrageenine. Evaluation has been carried out after 3, 12 and 24 hours. Butadion and diclofenac were used as control preparations, which are non-steroid anti-inflammatory preparations with analgesic and febrifugal activity. Said preparations have been orally administered to the animals in form of a suspension in starch mucus at the following doses: butadion—56 mg/kg and diclofenac—8 mg/kg.

The evaluation of the effect of the investigated substances included anti-inflammatory, analgesic and febrifugal activities. The general indices of the activity of the inflammatory process were evaluated by standardized biochemical and hematologic methods: ESR, levels of sialic acids, fibrinogen and content of leukocytes were determined. The febrifugal action of the preparations was evaluated by their capability to reduce the temperature of the skin of the rat paw at the nidus of inflammation.

The results of the performed investigations showed anti-inflammatory properties of the present agents at all doses. More pronounced activity has been found at the dose of 250 mg/kg, whereby the positive effect was maintained, and to some extent exceeded the effect of butadion and diclofenac at said dose.

Study of Anti-Inflammatory Activity in a Model of Formalin-Induced Arthritis in Rats The model of arthritis in animals was caused by injection of 0.1 ml of 2% formalin solution into the cavity of the knee joint. After 24 hrs a model of acute arthritis was obtained, which was suitable for studying the anti-inflammatory and anaesthetizing action of the preparations. Butadion and diclofenac were again used as control preparations. The present agent (3 doses) was dissolved in corn oil and administered according to the following regimen: 3 days prior to inflammation one time per day intraperitoneally (by a probe) and on the $4^{th}$ day 4 hours prior to the injection of formalin. The treatment was conducted over a period of 7 days by administering the investigated preparation one time per day. The evaluation of the results of treatment was conducted on the $4^{th}$ and $8^{th}$ day. Anti-inflammatory activity was estimated using the parameters of volume, pain sensitivity and inflammation temperature of the extremity. The total activity index was calculated (total percentages of decrease in size of the affected extremity for 7 days) and the therapeutic index (ratio of the total activity index of the preparation to the total activity index of the group with formalin).

With respect to the anaesthetizing and febrifugal activity the present agent exceeded the effect of butadion at all doses and it was practically not inferior to the effect of diclofenac at a dose of 250 mg/kg.

In the model of formalin arthritis, the talocrural joints of rats and gastric mucosa were also investigated. Histological sections included the zone of the joint with adjacent parts of bone tissue, surrounding soft tissues which are intimately connected to the joint including the adjacent derma, and in a series of observations also epidermis.

During the macroscopic inspection of the joints of the control group rats (formalin-induced arthritis without treatment) an enlargement of the joint and smoothening of its outlines were observed. At the incision periarticular tissues were edematic. A small quantity of unclear liquid occurred in the cavity of the joint. And the articulate surfaces of the cartilages were smooth. During the microscopic examination of the knee joint plethora and edema of periarticular tissues were observed, as well as changes in the synovial membrane, in the fibers of which the plethora, edema and lymphoid infiltration of areolar tissue of fibres were noted.

The joints of rats treated with the present agent did not show any pronounced macroscopic changes. Histologically, the synovial membrane, which lines the surface of the joint, consisted of less differentiated cells of connective tissue with round or oval nuclei. Plethoras or lymphoid infiltrations were not observed.

During the dissection of the experimental rats, the size and the shape of stomach and intestine did not show changes. The mucous membrane of the stomach body was bright, smooth and light pink. The lumen of the small intestine over the whole length was uniform. The mucous membrane of the small intestine was bright, smooth and light pink.

During the histological study of stomach and small intestine no destructive or inflammatory changes in the mucous membranes were noted. The epithelium of the mucous membrane of the small intestine did not show changes either.

Study of Anti-Inflammatory Activity in a Model of Formalin-Induced Arthritis in Rabbits Experiments were carried out on 51 rabbits "Chinchilla" having a weight of 2800-3200 g. The animals were divided into 3 groups: $1^{st}$ group—control animals (formalin arthritis), $2^{nd}$ group—administration of diclofenac at a dose of 8 mg/kg, $3^{rd}$ group—administration of the present agent at a dose of 250 mg/kg to investigated experimental formalin arthritis. An arthritis model was caused by administration of 0.1 ml of a 2% formalin solution into the cavity of the knee joint—and a model of acute arthritis was obtained after twenty-four hours.

The investigated agent and diclofenac were administered according to the following regimen: for preventive purposes 4 days prior to simulation of the arthritis on time per day intragastrically via a probe and on the $4^{th}$ day 4 hours prior to the administration of formalin. The treatment was conducted for a period of 7 days by administering the present agent and diclofenac one time per day.

Animals were euthanized under hexobarbital anesthesia after 3, 7 and 14 days after the induction of arthritis. Prior to beginning of the experiment and prior to euthanasia, blood was taken from the ear vein, and was used to determine hematologic parameters.

For a pathomorphological study, the joints were extracted together with the surrounding tissues and fixed in 10% neutral formalin.

The use of diclofenac substantially reduced the number of erythrocytes and hemoglobin in the peripheral blood in comparison with the initial level during all periods of observation. Generally, the use of the present agent did not have any considerable effect on the content of erythrocytes and hemoglobin. The hematocrit, which reflects the volume ratio of formed elements to the blood plasma, was reduced under the effect of diclofenac within the whole period of observation, especially at the $3^{rd}$ and $7^{th}$ days, whereas the present agent did not influence this parameter. The average content of hemoglobin in the erythrocyte is a derived index which reflects the state of the blood system. Said parameter was also decreased during the administration of diclofenac and did not change during the application of our agent. Thus, during the induction of formalin arthritis and as a result of its treatment with diclofenac, a clear tendency toward the development of an anaemic state was observed, whereas when treating with the present agent no substantial influence on the red blood parameters was observed. A decrease in the level of thrombocytes within the entire period of the study has been observed under the effect of diclofenac. Such decrease was not observed when using our agent. Under the effect of our agent and diclofenac the number of leukocytes was insignificantly reduced during all observation periods, the number of monocytes was not changed either, whereas the number of granulocytes was increased within all observation periods. Thus, the administration of diclofenac had a pronounced effect on the parameters of the peripheral blood, especially on the red cell number. No negative reactions on both the white and red blood cells were observed under the effect of our agent.

According to the results of the histological study of the joints inflammatory and destructive changes were observed under the effect of diclofenac, whereby generally the surface of articulate cartilages was affected. Inflammatory reaction was also found in articular bursa tissue. Blood vessels were extended and hyperemized in this region. 7 days after the administration of diclofenac articulate surfaces had uneven outlines and had affected the surface zone of articulate cartilages. 14 days after the administration of diclofenac, the surface of articulate cartilages was smoothed down, while irregularities were observed only in individual animals mostly in the peripheral parts of articulate surfaces.

Destructive changes were observed in the cartilages of articulate surfaces when treating with the present agent 3 days after the beginning of the experiment. which were however superficial and affected in general the outer zone of articulate cartilage. 7 days after the beginning of the experiment the destructive changes in the articulate cartilages were reduced in the group of animals our agent was administered to. Only in some instances small changes were observed in the form of irregularities in small parts of the cartilaginous surface closer to the articular bursa. The state of the articulate cartilages was completely normalized after 14 days of the administration of our agent. The surface of the articulate cartilages was even, smooth and without visible deformities and defects. Thus, during the administration of diclofenac, the inflammatory process calmed down later, in most of the animals in 14 days. During the administration of the present agent, destructive changes in the articulate cartilages and the surrounding tissues were reduced after 7 days.

Generally, according to the data of hematologic, biochemical and pathomorphological studies, the present agent possesses a pronounced anti-inflammatory, analgesic and febrifugal activity, comparable with the effect of diclofenac and butadion, while differing from the latter in terms of absence of undesirable side effects on the parameters of the peripheral blood and on the state of articulate cartilages.

Study of Other Properties of the Present Agent

The performed experimental investigations of general toxicity (acute, subacute, chronic and local irritating action), allergenicity and influence on the immune system have shown that the present preparation does not exibit toxic action on the organism of warm-blooded laboratory animals (rodents and dogs) under the conditions of acute and long-term administration in the course of 3 months.

The subacute (30 days) and chronic (90 days) daily administration of the preparation to experimental animals at doses which exceed those recommended for humans by 20-30 times did not exhibit a harmful effect on the main physiological systems (nervous, cardiovascular, hematopoietic, secretory, respiratory), metabolism, general well-being, development and the basic homeostatic parameters of the organism.

Since the main side action of synthetic anti-inflammatory preparations is their ulcerogenic action on the mucous membrane of the stomach, an advanced study has been carried out on the present agent in order to assess the possibility of said phenomenon. The performed investigations have shown that during both single (4000 mg/kg) and sub-chronic (800, 1600 and 4000 mg/kg) administration the preparation did not exibit an ulcerogenic action on gastric mucosa and intestine in rats. During the histological study of the stomach and the small intestine, no changes of inflammatory and destructive nature were observed. Moreover, the absence of an irritating action on the gastrointestinal tract wall is observed for both rodents and non-rodents, which indicates the general nature of the safety of the preparation.

The study of the influence of the preparation on the immune system has shown that it is possible to use it as an immunomodulator. By administration of the preparation at a dose of 20 mg/kg, the stimulation of the function can be expected more often, while when administering at a dose of 500 mg/kg a reduction in the intensity of immune reactions can be expected. The capability of the preparation to stimulate the important factor of non-specific resistance of phagocytes is revealed since at a dose of 500 mg/kg the number of phagocytizing cells was increased after its intragastric administration.

As a result of studying a possible allergenic effect of the preparation on both male and female guinea pigs it was shown that it does not cause a general anaphylactic reaction. Conjunctival tests, mast cell degranulation reactions and reactions of immune complexes were negative. These data make it possible to conclude that the present preparation does not possess an allergizing action in case of intragastric administration.

In animals having immunodepression caused by emotional stress (long-term congestion), the disturbance of the development of a humoral immune response and the reduction in the functional activity of macrophages were prevented by intragastric administration of the preparation at a dose of 500 mg/kg for 10 days.

Thus, the complex preparation according to the present invention, which contains dry *Boswellia* extract in Siberian stone pine and *Curcuma* root oil extract as basic active components, possesses a pronounced anti-inflammatory activity, qualitatively differing from nonsteroid agents in terms of an absence of ulcerogenicity and the presence of immunomodulating and antioxidant activity, which indicate an increase in the protective functions of the organism.

INDUSTRIAL APPLICABILITY

The present preparation can be recommended for combination therapy of different inflammatory diseases such as arthritis, osteoarthrosis, rheumatoid arthritis, post-traumatic pain syndrome, and also in the form of a biologically active food supplement as overall-strengthening agent.

The invention claimed is:

1. An anti-inflammatory agent formulated in a gelatin capsule containing lecithin, butyl hydroxyl toluene, alpha-tocopherol acetate, ascorbyl palmitate, dry extract of Boswellia, and an oil extract of Siberian stone pine seeds and Curcuma roots in the following amounts, in mg/capsule:

| | |
|---|---|
| dry extract of *Boswellia* | 25-35 |
| oil extract of Siberian stone pine seed and *Curcuma* roots | 250-280 |
| alpha tocopherol acetate | 0.30-0.35 |
| ascorbyl palmitate | 0.75-0.85 |
| lecithin | 0.15-0.25 |
| butyl hydroxyl toluene | 0.01-0.02, | wherein said oil extract of Siberian stone pine seeds and Curcuma roots is made by a method comprising soaking intact Siberian stone pine seeds in a water-alcoholic solution, mixing said seeds with a vegetable oil carrier and subsequently extracting the seeds to obtain a pine seed oil extract, pre-grinding and screening Curcuma roots, mixing said roots with the pine seed oil extract, and extracting to obtain an oil extract of Siberian stone pine seeds and Curcuma roots.

2. The agent according to claim 1, wherein the vegetable oil carrier is corn, soybean, or sunflower oil.

3. The agent of claim 1, wherein said oil extract of Siberian stone pine seeds and Curcuma roots is made by a method comprising soaking intact Siberian stone pine seeds in a water-alcoholic solution, mixing said seeds with a vegetable oil carrier at a volume ratio not more than 1:20, subsequently extracting the seeds to a pine seed oil extract, pre-grinding and screening Curcuma roots, mixing said roots with the pine seed oil extract at a volume not more than 1:10, and extracting to obtain an oil extract of Siberian stone pine seeds and Curcuma roots.

4. The agent of claim 3, wherein the extracting of the components is carried out by means of a rotary-pulsation method at a temperature of not more than 50° C. and is followed by settling and filtering the oil extract.

5. A method for producing the anti-inflammatory agent according to claim 1, comprising soaking intact Siberian stone pine seeds in a water-alcoholic solution, mixing said seeds with a vegetable oil carrier at a volume of not more than 1:20, subsequently extracting the pine seeds to obtain a pine seed oil extract, pre-grinding and screening Curcuma roots, mixing said roots with the pine seed oil extract at a volume of not more than 1:10 and extracting to obtain an oil extract of Siberian stone pine seeds and Curcuma roots, mixing 250 to 280 mg of the oil extract of Siberian stone pine seeds and Curcuma roots with 25-35 mg of a dry Boswellia extract, 0.30-0.35 mg of alpha-tocopherol acetate, 0.75-0.85 mg of ascorbyl palmitate, 0.15-0.25 mg of lecithin and 0.01-0.02 mg of butyl hydroxyl toluene and formulating in a gelatin capsule.

6. The method according to claim 5, wherein the extracting of the components is carried out by means of a rotary-pulsation method at a temperature not more than 50° C. and is followed by settling and filtering the oil extracts.

* * * * *